US009445768B2

(12) United States Patent
Alexander et al.

(10) Patent No.: US 9,445,768 B2
(45) Date of Patent: Sep. 20, 2016

(54) PERSONAL BIOSENSOR ACCESSORY ATTACHMENT

(71) Applicant: NeuroSky, Inc., San Jose, CA (US)

(72) Inventors: Zavier Alexander, San Jose, CA (US); Cheng-I Chuang, Saratoga, CA (US)

(73) Assignee: NeuroSky, Inc., San Jose, CA (US)

( * ) Notice: Subject to any disclaimer, the term of this patent is extended or adjusted under 35 U.S.C. 154(b) by 0 days.

(21) Appl. No.: 14/076,753

(22) Filed: Nov. 11, 2013

(65) Prior Publication Data

US 2014/0148715 A1 May 29, 2014

Related U.S. Application Data

(60) Provisional application No. 61/731,348, filed on Nov. 29, 2012.

(51) Int. Cl.
*A61B 5/00* (2006.01)
*A61B 5/0408* (2006.01)
*A61B 5/0478* (2006.01)
*A61B 5/0492* (2006.01)
*A61B 5/0496* (2006.01)

(52) U.S. Cl.
CPC ........... *A61B 5/6898* (2013.01); *A61B 5/0408* (2013.01); *A61B 5/0478* (2013.01); *A61B 5/0492* (2013.01); *A61B 5/0496* (2013.01); *A61B 2560/0406* (2013.01); *A61B 2560/0443* (2013.01); *A61B 2560/0468* (2013.01)

(58) Field of Classification Search
CPC .............. A61B 2560/0406; A61B 2560/0443; A61B 2560/0468; A61B 5/0404; A61B 5/0408; A61B 5/0476; A61B 5/0478; A61B 5/0488; A61B 5/0492; A61B 5/0496; A61B 5/053

USPC ................. 600/383, 544, 546, 547
See application file for complete search history.

(56) References Cited

U.S. PATENT DOCUMENTS

| | | | | |
|---|---|---|---|---|
| 8,301,232 B2* | 10/2012 | Albert | ............ | A61B 5/0006 600/509 |
| 8,311,769 B2* | 11/2012 | Yuen | ............ | A61B 5/0002 702/160 |
| 8,311,770 B2* | 11/2012 | Yuen | ............ | A61B 5/0002 702/160 |
| 8,509,882 B2* | 8/2013 | Albert | ............ | A61B 5/0404 600/509 |
| 8,639,288 B1* | 1/2014 | Friedman | ............ | A61M 5/20 455/556.1 |
| 8,751,039 B1* | 6/2014 | Macoviak et al. | ............ | 700/244 |
| 9,026,202 B2* | 5/2015 | Albert | ............ | A61B 5/0452 600/513 |
| 2004/0039254 A1 | 2/2004 | Stivoric et al. | | |
| 2004/0193068 A1* | 9/2004 | Burton | ............ | A61B 5/0476 600/544 |

(Continued)

FOREIGN PATENT DOCUMENTS

| JP | 2009160091 | 7/2009 |
|---|---|---|
| WO | 0107993 | 2/2001 |

(Continued)

*Primary Examiner* — Christopher A Flory
(74) *Attorney, Agent, or Firm* — Van Pelt, Yi & James LLP

(57) ABSTRACT

Techniques for providing a personal biosensor accessory attachment are disclosed. In some embodiments, a personal biosensor accessory attachment system is disclosed. In some embodiments, a personal biosensor accessory attachment system includes a biosensor for detecting a bio-signal; and a personal biosensor device that is adapted to securely hold the biosensor, in which the personal biosensor device can be adapted to be mechanically secured to a plurality of computing devices.

14 Claims, 6 Drawing Sheets

(56) References Cited

U.S. PATENT DOCUMENTS

| | | |
|---|---|---|
| 2005/0090754 A1 | 4/2005 | Wolff et al. |
| 2005/0234312 A1* | 10/2005 | Suzuki .................. A61B 5/103 600/300 |
| 2006/0123053 A1* | 6/2006 | Scannell, Jr. .............. 707/104.1 |
| 2007/0085690 A1* | 4/2007 | Tran ...................... A61B 5/103 340/573.1 |
| 2007/0265533 A1* | 11/2007 | Tran ...................... A61B 5/021 600/481 |
| 2007/0276270 A1* | 11/2007 | Tran ...................... A61B 5/0022 600/508 |
| 2007/0287596 A1* | 12/2007 | Case et al. ......................... 482/8 |
| 2008/0001735 A1 | 1/2008 | Tran |
| 2008/0004904 A1* | 1/2008 | Tran .................... A61B 5/0006 705/2 |
| 2008/0097552 A1 | 4/2008 | Dicks et al. |
| 2008/0177197 A1 | 7/2008 | Lee et al. |
| 2008/0262335 A1 | 10/2008 | Sun et al. |
| 2008/0294019 A1* | 11/2008 | Tran .................... A61B 5/0006 600/301 |
| 2008/0294031 A1 | 11/2008 | Wilson et al. |
| 2009/0023428 A1* | 1/2009 | Behzad et al. ............. 455/414.3 |
| 2009/0214060 A1* | 8/2009 | Chuang et al. ................ 381/151 |
| 2009/0281408 A1* | 11/2009 | Lee et al. ................... 600/372 |
| 2009/0326354 A1* | 12/2009 | Mao .................. A61B 5/14532 600/344 |
| 2009/0326406 A1* | 12/2009 | Tan ......................... G06F 1/163 600/546 |
| 2010/0042008 A1 | 2/2010 | Amitai et al. |
| 2010/0076333 A9* | 3/2010 | Burton ................ A61B 5/0476 600/544 |
| 2010/0234752 A1* | 9/2010 | Sullivan et al. ............. 600/544 |
| 2010/0331649 A1 | 12/2010 | Chou |
| 2011/0015496 A1* | 1/2011 | Sherman ............... A61B 5/0006 600/301 |
| 2011/0040202 A1* | 2/2011 | Luo et al. ..................... 600/544 |
| 2011/0130675 A1* | 6/2011 | Bibian ................ A61B 5/0476 600/544 |
| 2011/0137144 A1 | 6/2011 | Rofougaran et al. |
| 2011/0300847 A1 | 12/2011 | Quy |
| 2011/0301435 A1* | 12/2011 | Albert .................. A61B 5/0404 600/301 |
| 2011/0301439 A1* | 12/2011 | Albert .................. A61B 5/6898 600/301 |
| 2011/0306859 A1 | 12/2011 | Saldivar et al. |
| 2012/0092157 A1* | 4/2012 | Tran .................... G06F 19/3418 340/539.12 |
| 2012/0172682 A1* | 7/2012 | Linderman .......... A61B 5/0476 600/301 |
| 2012/0172689 A1 | 7/2012 | Albert et al. |
| 2012/0188158 A1* | 7/2012 | Tan ...................... A61B 5/0488 345/156 |
| 2012/0197092 A1 | 8/2012 | Luo et al. |
| 2012/0220889 A1* | 8/2012 | Sullivan et al. ............. 600/544 |
| 2012/0238845 A1* | 9/2012 | Yang .................... A61B 5/6804 600/322 |
| 2012/0242501 A1* | 9/2012 | Tran .................... A61B 5/0024 340/870.02 |
| 2012/0245450 A1* | 9/2012 | Lee et al. ....................... 600/383 |
| 2012/0250197 A1* | 10/2012 | Sullivan ......................... 361/56 |
| 2012/0295589 A1 | 11/2012 | Alexander et al. |
| 2012/0316456 A1 | 12/2012 | Rahman et al. |
| 2013/0331663 A1* | 12/2013 | Albert .................. A61B 5/0404 600/301 |
| 2014/0066798 A1* | 3/2014 | Albert .................. A61B 5/0452 600/513 |
| 2014/0228665 A1* | 8/2014 | Albert .................. A61B 5/6898 600/384 |
| 2014/0305204 A1* | 10/2014 | Hong .................... A61B 5/7455 73/504.08 |
| 2015/0122018 A1* | 5/2015 | Yuen ...................... G01B 21/16 73/384 |
| 2015/0196256 A1* | 7/2015 | Venkatraman ......... A61B 5/721 600/301 |

FOREIGN PATENT DOCUMENTS

| | | |
|---|---|---|
| WO | 03005173 | 1/2003 |
| WO | 2008147909 | 12/2008 |
| WO | 2012158457 | 11/2012 |

* cited by examiner

PERSONAL BIOSENSOR ACCESSORY ATTACHMENT

CROSS REFERENCE TO OTHER APPLICATIONS

This application claims priority to U.S. Provisional Patent Application No. 61/731,348 entitled PERSONAL BIOSENSOR ACCESSORY ATTACHMENT filed Nov. 29, 2012, which is incorporated herein by reference for all purposes.

BACKGROUND OF THE INVENTION

Biosensors (e.g., bio-signal sensor chips) exist and can be used to enable bio-signal features in various product categories. For example, consumer products are being developed to use such biosensor technology.

BRIEF DESCRIPTION OF THE DRAWINGS

Various embodiments of the invention are disclosed in the following detailed description and the accompanying drawings.

DETAILED DESCRIPTION

Figure 1:
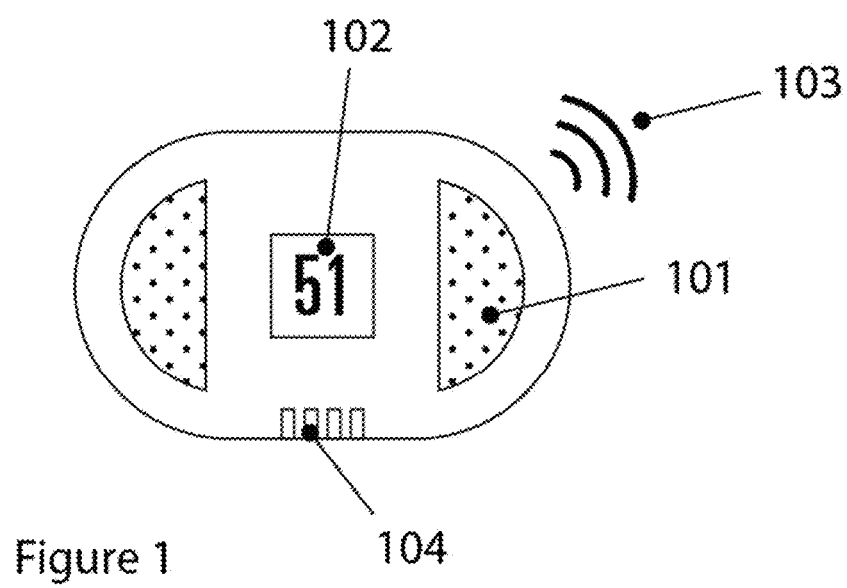
FIG. 1 illustrates a personal biosensor device in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Bioelectric signals are electrical signals that can be generated by living cells, tissues, or organisms. Bioelectric signals can be measured using bioelectric signal sensors, such as electrodes. For example, electrodes can be mounted on the surface of the body to measure various types of bioelectric signals. Bioelectric signals produced by the brain are referred to as electroencephalography (EEG) signals. Bioelectric signals produced by the heart are referred to as electrocardiography (ECG) signals. Bioelectric signals produced by the muscles are referred to as electromyography (EMG) signals. Bioelectric signals produced by the eyes are referred to as electrooculography (EOG) signals.

Products embedded with biosensors can provide value for users in the form of on-demand ubiquitous personal bio-data for health and wellness, entertainment, and/or other uses. As a quickly developing emerging technology, it is not always possible to incorporate the latest personal biosensors into the design cycle of a mass produced product.

What are needed are new and improved techniques for providing biosensors that can be used with existing devices (e.g., portable computing devices, such as smart phones, tablets, etc.).

Accordingly, various techniques for providing a personal biosensor accessory attachment are disclosed. In some embodiments, a personal biosensor accessory attachment system is disclosed. In some embodiments, such a system allows for the convenient addition of bio-sensing capabilities to products, which otherwise lack these features or allows for products with limited sensing capabilities to be augmented.

In some embodiments, a personal biosensor accessory attachment system includes a biosensor for detecting a bio-signal; and a personal biosensor device that is adapted to securely hold the biosensor, in which the personal biosensor device can be adapted to be mechanically secured to a plurality of computing devices (e.g., a mobile computing device, such as a mobile phone or a tablet computer). In some embodiments, the personal biosensor accessory attachment system further includes a fastening device that can be adapted for securely connecting the personal biosensor device to the plurality of computing devices. For example, the fastening device can include one or more additional biosensors for detecting a bio-signal.

In some embodiments, the personal biosensor device further includes a display output for providing an output feedback for bio-signal related information measured using the biosensor. In some embodiments, the personal biosensor device further includes an audio output for providing an output feedback for bio-signal related information measured using the biosensor. In some embodiments, the personal biosensor device further includes a communication mechanism for providing wired or wireless communication based on bio-signal related information measured using the biosensor to the computing device. In some embodiments, the personal biosensor device further includes a communication mechanism for providing wired or wireless communication based on bio-signal related information measured using the biosensor to a cloud-based bio-signal monitoring service.

In some embodiments, the personal biosensor device that is adapted to securely hold a plurality of biosensors includes one or more of each of the following types of biosensors: an electroencephalography (EEG) sensor, an electrocardiography (ECG) sensor, an electrooculography (EOG) sensor, an electromyography (EMG) sensor, and a galvanic skin response (GSR) sensor. In some embodiments, the biosensor includes an EEG sensor, in which the EEG sensor includes a stainless steel passive, dry biosensor. In some embodiments, the biosensor measures an EEG signal, in which the EEG signal is processed to determine a user's mental state (e.g., whether a user is in a focused state or in a relaxed state).

FIG. 1 illustrates a personal biosensor device in accordance with some embodiments. As shown, the personal biosensor device includes biosensors (e.g., bio-signal sensors) for EEG, ECG, EMG, blood oximetry, and/or other types of biosensors; a user feedback mechanism in the form of a screen display (e.g., an LCD screen), LEDs, vibration, and/or an audio speaker; the ability to communicate with other devices through a physical port, such as a USB or wirelessly through radio frequency or infrared (e.g., Bluetooth wireless communication standard or other wireless communication standards or protocols). In particular, the personal biosensor device is designed to be mechanically secured to another accessory, which will change the specific utility scenario of the sensor unit. For example, the sensor unit can be secured to a mobile phone (e.g., a smart phone), to a chest strap for sensing ECG, or to a clip, which can allow the user to fasten the sensor unit to an article of clothing. As another example, the sensor unit can be secured to a watch, a keyboard, an article of clothing, or a piece of jewelry (e.g., a bracelet that a user wears on their wrist).

As shown in FIG. 1, the personal biosensor device includes a bio-sensor or bio-sensors (e.g., ECG, EEG, EMG, blood oximetry, and/or types of biosensors) (101), a user feedback mechanism (e.g., LCD Screen, LED array, audio speakers, and/or other output mechanisms) (102), and communication equipment for sending bio-signal data to another device (e.g., USB port, pin contacts, and/or wireless radio frequency, such as Bluetooth and/or other protocols/standards for wireless communications) (103, 104). For example, the biosensor device can also include an internal flash memory and/or processing capability. In some embodiments, the form factor of the biosensor device is designed to allow mechanical fastening directly to another product or with a specifically designed fastening device.

Figure 2:
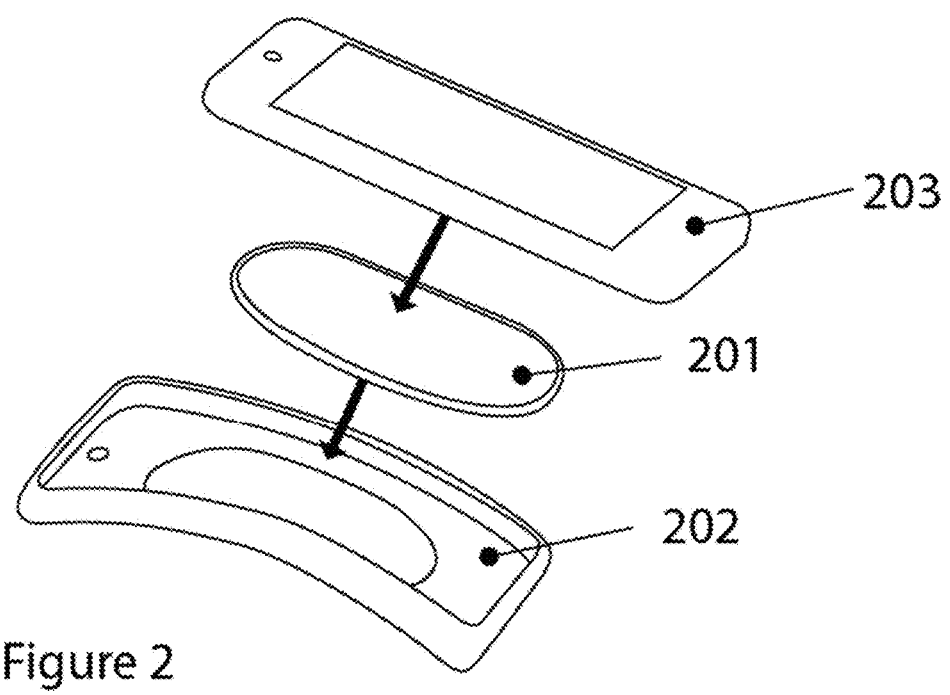
FIG. 2 illustrates a method for a sensor unit to be attached to a mobile device, which it communicates with by utilizing a third mechanical part to fasten it within close physical distance in accordance with some embodiments.

FIG. 2 illustrates a method for a sensor unit to be attached to a mobile device, which it communicates with by utilizing a third mechanical part to fasten it within close physical distance in accordance with some embodiments. For example, the mechanical fastening device can be a cast silicon or rubber part or have embedded sensors and other electronics, which can connect to the sensor unit and assist in gathering or displaying bio-signal information. The fastening device securely holds the biosensor device.

In particular, FIG. 2 illustrates the assembly of the sensor unit (201), mobile device (203), and fastening device (202) used to keep the sensor unit and the mobile device in close proximity to facilitate wired or wireless communication.

The fastening device may not be necessary in all embodiments or user interaction scenarios. For example, the biosensor device can be used by itself, or the biosensor device and mobile device or other computing unit can be geographically separated. The fastening device can also secure the biosensor device to another mobile or computing device. As another example, the fastening device can only be a clip that helps the user fasten the biosensor device onto clothes. As yet another example, the fastening device can be in the form of a strap, which would help ensure constant sensor contact on the user's chest, limb, head, or other location of the user's body.

In some embodiments, there is no fastening device, and the biosensor device communicates directly to a mobile or other computing device through a USB cable, wireless RF, or through an Internet-based cloud service. In some embodiments, the sensor device or fastening device interacts directly with the mobile device or each other as a source of power (e.g., extra battery, wireless magnetic induction charging, solar charging, or kinetic charging) or includes memory, which stores bio-signal data and/or miscellaneous user data in the same manner as an all-purpose USB memory stick. For example, transfer of data to the sensor device or fastening device with additional memory capability is not limited to physical interfaces like a USB stick and can include wireless data transmission, such as radio frequency (e.g., Bluetooth), infrared light, or digital audio pulses.

In some embodiments, a fastening device is passive without any electronics or sensor contacts. In some embodiments, a fastening device is active with sensor contacts and/or electronics. For example, the display, audio, communication and power supply/recharging, and/or other functions can be on the biosensor device and/or the fastening device. In some embodiments, the fastening device performs one or more active functions, and an electrical connection between the biosensor device and the fastening device can be through dedicated connectors and/or through the sensor contacts on the biosensor device.

Figure 3:
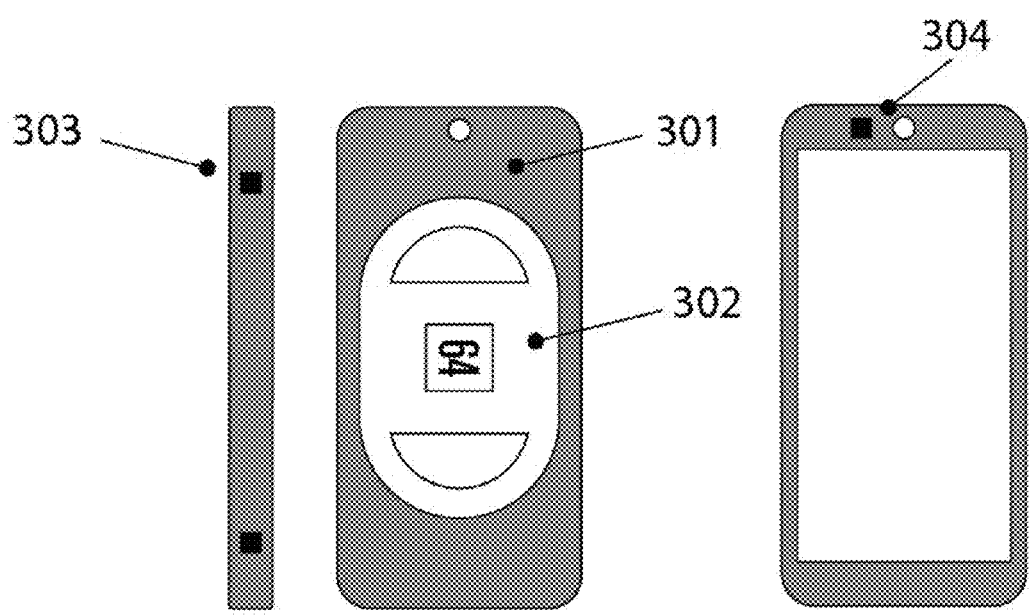
FIG. 3 illustrates the sensor unit, mobile device, and fastening device assembled together in accordance with some embodiments.

FIG. 3 illustrates the sensor unit, mobile device, and fastening device assembled together in accordance with some embodiments. As shown, there are additional sensors on the fastening device, which connect to the sensor unit to enhance or change the nature of the bio-signal captured. The additional sensors connect physically to the sensors on the biosensor device through extended electrical leads. In some embodiments, sensors are provided that connect to the communication port of the biosensor device or wirelessly.

In particular, FIG. 3 illustrates the biosensor device (302), mobile device and fastening device (301) assembled together. Additional sensors (303, 304) on the fastening device connect to the biosensor device through a physical electrical or wireless digital connection. In some embodiments, the fastening device is inert with no sensors or embedded electronics. Sensors on the fastening device may differ from those on the biosensor device. For example, the biosensor device can include ECG sensor(s) while the sensors on the fastening device can include EEG sensor(s). Sensors on the fastening device can also increase the capabilities of the biosensor device by adding additional sensors of the same kind (e.g., adding additional EEG sensors to allow for more complex algorithms to be used) or be made from different/superior materials to influence the quality of the bio-signal captured.

Figure 4:
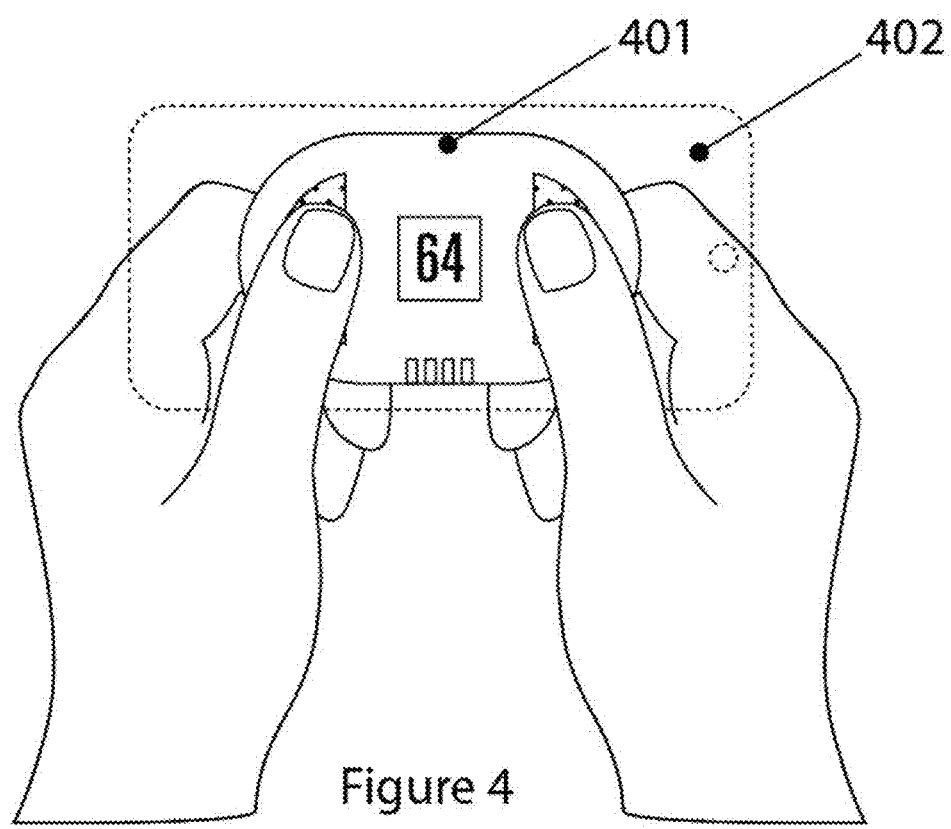
FIG. 4 illustrates a configuration of the sensor unit, mobile device, and fastening device in use (e.g., or just the sensor unit by itself) in accordance with some embodiments.

FIG. 4 illustrates a configuration of the sensor unit, mobile device, and fastening device in use (e.g., or just the sensor unit by itself) in accordance with some embodiments. As shown, the user can touch two bio-sensor pads. For example, the sensor unit can communicate the collected data to the mobile device for display or to be stored, and the sensor unit can also display the bio-signal data on the sensor unit itself.

In particular, FIG. 4 illustrates one use case scenario in which the user touches two ECG biosensors with their thumbs on the biosensor device (401), which is attached to the back of a mobile phone. As shown, an LCD screen on the biosensor device gives the user visual feedback on the user's heart rate measured using the two ECG biosensors. The biosensor device can be used alone or attached to another device. The fastening device (402) is optional in this case. In some embodiments, the biosensor device displays complex graphical representations of the bio-signal information, simple LED lights and patterns or audio tones, vibrations, heat, music, or voice to convey meaningful feedback to the user.

Figure 5:
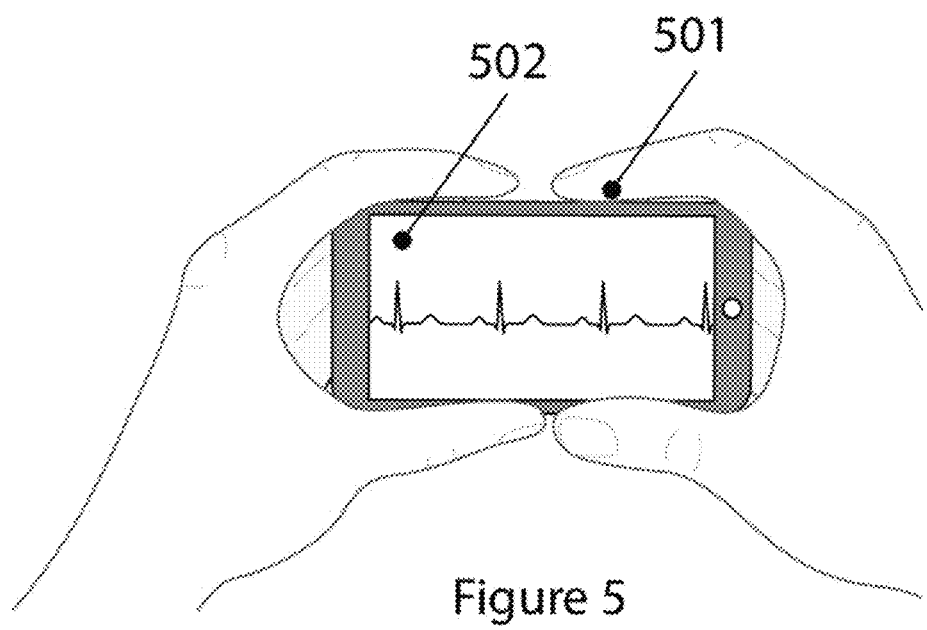
FIG. 5 illustrates a configuration of a personal biosensor device in which the user touches bio-sensors located on the mechanical fastening device that connect back to the sensor unit in accordance with some embodiments.

FIG. 5 illustrates a configuration of a personal biosensor device in which the user touches bio-sensors located on the mechanical fastening device that connect back to the sensor unit in accordance with some embodiments. As shown, the sensor unit collects the bio-signal data from the sensors on the fastening device and sends the data to a mobile device for display.

In particular, FIG. 5 illustrates another scenario in which the user contacts bio-sensors (501) located on the fastening device to facilitate a different hand orientation when using the device. The bio-signal data is collected by the sensors on the fastening device, communicated to the biosensor device, and sent to the mobile device. The mobile device processes, stores, and displays the bio-signal information (502) to the user. For example, bio-signal information can be displayed on the device in closest proximity to the biosensor device or with other mobile devices simultaneously over wired, wireless, or Internet communications. In some embodiments, the bio-signal sensors are positioned or located on the fastening device so as to facilitate contact with different areas of the user's body or be designed to contact multiple individual users at once.

Figure 6:
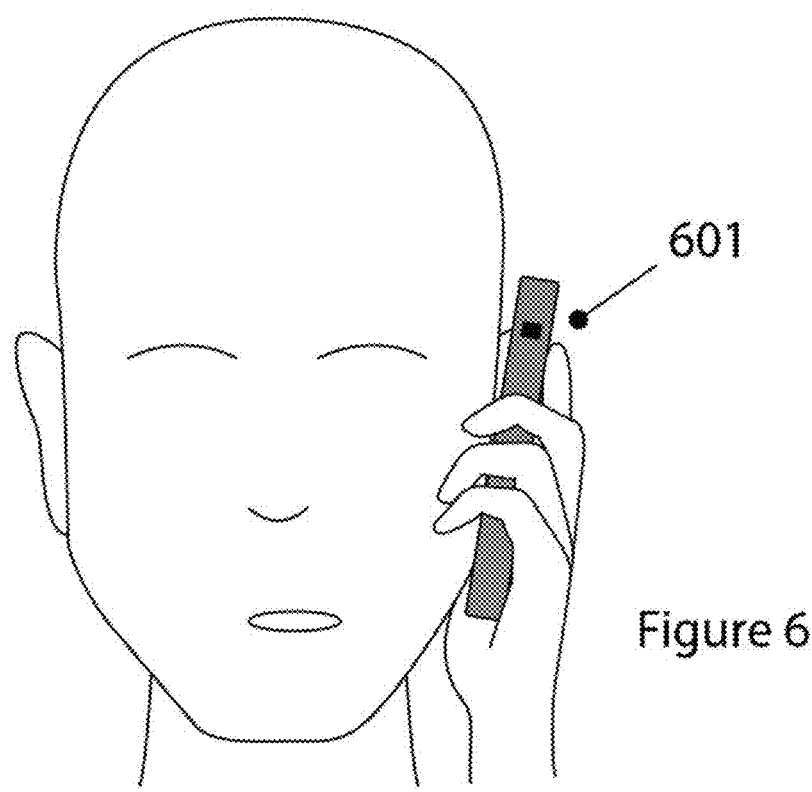
FIG. 6 illustrates a configuration of a personal biosensor device in which a sensor on the fastening device is located such that it contacts another area of the human body of a user instead of the hand of the user for passive data collection while the user is actively engaged in another activity in accordance with some embodiments.

FIG. 6 illustrates a configuration of a personal biosensor device in which a sensor on the fastening device is located such that it contacts another area of the human body of a user instead of the hand of the user for passive data collection while the user is actively engaged in another activity in accordance with some embodiments.

In particular, FIG. 6 illustrates another configuration in which the biosensors are located on the fastening device, but positioned so that the location of the biosensors facilitates contact with the user's face (601) when the user is holding the mobile phone for a phone call. Additional sensors on the fastening device collect ECG data when the user is actively engaged in talking and not viewing the data.

In some embodiments, the fastening device is designed to facilitate placing the sensor unit on a chest strap, clothing, hat, gloves, shoes, and/or other personal apparel or articles of clothing. In some embodiments, the fastening device is designed to facilitate placing the sensor unit on stationary devices that the user comes into contact with, such as exercise equipment, vehicle steering wheels, furniture, or architectural features such as door handles or floors.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for a personal biosensor accessory attachment system, comprising:
    a first biosensor for detecting a first bio-signal, wherein the first biosensor includes an electroencephalography (EEG) sensor, an electrocardiography (ECG) sensor, an electrooculography (EOG) sensor, an electromyography (EMG) sensor, or a galvanic skin response (GSR) sensor;
    a personal biosensor device that is adapted to securely hold the first biosensor; and
    a fastening device that can be adapted for securely connecting the personal biosensor device to a plurality of computing devices, wherein the fastening device includes a second biosensor for detecting a second bio-signal, the first bio-signal being different from the second bio-signal, wherein the second biosensor includes an electroencephalography (EEG) sensor, an electrocardiography (ECG) sensor, an electrooculography (EOG) sensor, an electromyography (EMG) sensor, or a galvanic skin response (GSR) sensor;
    wherein the fastening device includes a cast silicon or rubber part;
    wherein the second biosensor corresponds to the same kind of biosensor as the first biosensor to increase the quality of the first bio-signal detected; and
    wherein the personal biosensor device is adapted to be mechanically secured to the plurality of computing devices.

2. The system recited in claim 1, wherein the personal biosensor device further comprises:
    a display output for providing an output feedback for bio-signal related information measured using the first biosensor.

3. The system recited in claim 1, wherein the personal biosensor device further comprises:
    an audio output for providing an output feedback for bio-signal related information measured using the first biosensor.

4. The system recited in claim 1, wherein the personal biosensor device further comprises:
    a communication mechanism for providing wired or wireless communication based on bio-signal related information measured using the first biosensor to the plurality of computing devices.

5. The system recited in claim 1, wherein the personal biosensor device further comprises:
    a communication mechanism for providing wired or wireless communication based on bio-signal related information measured using the first biosensor to a cloud-based bio-signal monitoring service.

6. The system recited in claim 1, wherein the EEG sensor includes a stainless steel passive, dry biosensor.

7. The system recited in claim 1, wherein the first biosensor measures an EEG signal, and wherein the EEG signal is processed to determine a user's mental state.

8. The system recited in claim 1, wherein the plurality of computing devices includes a mobile computing device.

9. The system recited in claim 1, wherein the plurality of computing devices includes a mobile phone or a tablet computer.

10. The system recited in claim 1, wherein the plurality of computing devices includes a watch.

11. The system recited in claim 1, wherein the first biosensor is attached, via the fastening device, to an article of clothing.

12. The system recited in claim 1, wherein the first biosensor is attached, via the fastening device, to a piece of jewelry.

13. The system recited in claim 1, wherein the second biosensor is made of a different material than the material of the first biosensor to enhance the quality of the first biosignal detected.

14. The system recited in claim 1, wherein the fastening device interacts directly with the plurality of computing devices as a source of power, the source of power including an extra battery, wireless magnetic induction charging, solar charging, or kinetic charging.

* * * * *